United States Patent [19]

Young et al.

[11] Patent Number: 4,618,738

[45] Date of Patent: Oct. 21, 1986

[54] HYDROCARBON CONVERSION PROCESS WITH CATALYTICALLY ACTIVE AMORPHOUS SILICA

[75] Inventors: Dean A. Young, Yorba Linda; Jeffery W. Koepke, La Habra, both of Calif.

[73] Assignee: Union Oil Company of California, Los Angeles, Calif.

[21] Appl. No.: 760,077

[22] Filed: Jul. 29, 1985

Related U.S. Application Data

[62] Division of Ser. No. 645,920, Aug. 29, 1984, Pat. No. 4,548,705, which is a division of Ser. No. 526,866, Aug. 25, 1983, Pat. No. 4,481,102, which is a division of Ser. No. 356,351, Mar. 9, 1982, Pat. No. 4,414,137.

[51] Int. Cl.$^4$ ............................................. C07C 5/22
[52] U.S. Cl. .................................. 585/480; 208/111; 208/120
[58] Field of Search ........................................ 585/480

[56] References Cited

U.S. PATENT DOCUMENTS

| | | | |
|---|---|---|---|
| 2,741,646 | 4/1956 | Clark | 208/134 |
| 3,493,341 | 2/1970 | Le Page et al. | 502/243 |
| 3,556,725 | 1/1971 | Chiola et al. | 423/329 |
| 4,061,724 | 12/1977 | Grose et al. | 423/335 |
| 4,073,865 | 2/1978 | Flanigen et al. | 423/335 |
| 4,270,017 | 5/1981 | Young | 585/437 |
| 4,283,306 | 8/1981 | Herkes | 502/202 |
| 4,325,929 | 4/1982 | Young | 423/339 |
| 4,344,927 | 8/1982 | Young | 423/339 |
| 4,414,137 | 11/1983 | Young et al. | |
| 4,428,825 | 1/1984 | Ward et al. | |
| 4,428,862 | 1/1984 | Ward et al. | |
| 4,481,102 | 11/1984 | Young et al. | |
| 4,501,925 | 2/1985 | Young et al. | |
| 4,513,158 | 4/1985 | Young et al. | |

FOREIGN PATENT DOCUMENTS

| | | |
|---|---|---|
| 495053 | 9/1978 | Australia. |
| 35807 | 9/1981 | European Pat. Off. |

OTHER PUBLICATIONS

"Amorphous Silica" by P. K. Maher set forth in the Kirk-Othmer Encyclopedia of Chemical Technology, 2nd ed., vol. 18, pp. 61-72, (1969).

"High Surface Area Amorphous Silica-Alumina Cracking Catalysts with Controlled Site Spacings" by M. R. S. Manton, set forth Feb., 1978, by the Council for Scientific and Industrial Research, South Africa.

"Crystalline Silicic Acids and Their Interface Reactions" by G. Lagaly set forth in Advances in Colloid and Interface Science, vol. 11, pp. 105-148 (1979).

"Stable Si-H Groups on Silica Surfaces" by Morterra and Low set forth in Chemical Communications, p. 203 (1968).

"Reactive Silica, VIII. Methoxylation of Silica Using Trimethoxymethane" by Low and Mark set forth in Journal of Catalysis, vol. 44, pp. 300-305 (1976).

"Reactive Silica. XII. The Sorption and Polymerization of Several Alkenes" by Low and Mark set forth in Journal of Catalysis, vol. 50, pp. 373-378 (1977).

"Reactive Silica. X. Ethylene Sorption and Polymerization of Several Alkenes" by Low and Mark set forth in Journal of Catalysis, vol. 48, pp. 104-110 (1977).

"Reactive Silica. XIII. Activation of Silica by Pyrolizing Chemisorbed HSiCl$_3$" by Low and Mark set forth in Journal of Catalysis, vol. 54, pp. 219-222 (1978).

"Some Quaternary Ammonium Silicates" by Merrill and Spencer set forth in Journal of Physical and Colloidal Chemistry, vol. 55, pp. 187-195 (1951).

"Catalytic Properties of Attrition Ground Silica" by Hatcher, Jr., et al., set forth in Journal of Catalysis, vol. 38, pp. 73-79 (1975).

"Reactive Silica. I. The Formation of a Reactive Silica by the Thermal Collapse of the Methoxy Groups of Methylated Aerosil" by Morterra and Low set forth in the Journal of Physical Chemistry, vol. 73, No. 2, pp. 321-326, Feb. (1969).

"Reactive Silica. II. The Nature of the Surface Silicon Hydrides Produced by the Chemisorption of Hydrogen" by Morterra and Low set forth in the Journal of Physical Chemistry, vol. 73, No. 2, pp. 327-333, Feb. (1969).

"Infrared Study of Surface Modes on Silica" by Boccuzzi et al., set forth in the Journal of Physical Chemistry, vol. 82, No. 11, pp. 1298-1303 (1978).

Primary Examiner—Curtis R. Davis
Attorney, Agent, or Firm—Dean Sandford; Gregory F. Wirzbicki; Alan H. Thompson

[57] ABSTRACT

Catalytically active amorphous silicas are prepared by dehydrating a silica hydrogel or precipitate prepared from an acidified aqueous silicate solution containing an amine of pK$_a$ above 10 or a cation containing either a nitrogen or phosphorus atom bonded to four carbon atoms. The resultant amorphous silica is catalytically active for, among other chemical reactions, the isomerization of orthoxylene and the cracking of hydrocarbons.

25 Claims, No Drawings

HYDROCARBON CONVERSION PROCESS WITH CATALYTICALLY ACTIVE AMORPHOUS SILICA

RELATED APPLICATIONS

This application is a division of application Ser. No. 645,920, filed Aug. 29, 1984, now U.S. Pat. No. 4,548,705 which is a divisional application of U.S. patent application Ser. No. 526,866, filed Aug. 25, 1983, now U.S. Pat. No. 4,481,102 which is divisional application of U.S. application Ser. No. 356,351, filed Mar. 9, 1982, and now U.S. Pat. No. 4,414,137.

BACKGROUND OF THE INVENTION

This invention relates to amorphous silica and most especially to silica gels useful in catalysis. The invention also relates to a method for preparing such silica gels, and to catalytic processes wherein the gels are utilized as catalysts or catalyst components.

Silica gel is but one of several forms of amorphous silica and, like the other forms, is an essentially anhydrous polymer of silica. Silica gel may be prepared in a number of ways, one of which is to form an aqueous silicate solution, usually an aqueous sodium silicate solution, followed by acidifying the solution to form a silica gel (or silica xerogel) product. Alternatively, one may form the gel by removal of the cation associated with the silicate anion by ion exchange, followed by drying of the resultant hydrogel.

The formation of the hydrogel, by ion exchanging, acidifying, or otherwise destabilizing an aqueous silicate solution, is caused by a polymerization reaction that may be visualized as the formation of a silica network which envelops water like a sponge. Upon heating, the water is removed, leaving microscopic cavities or pores in the locations formerly occupied by water. The resulting product, termed either a silica gel or silica xerogel, is highly useful, as for example as an adsorbent in gas masks or as a desiccant.

As is the case with many crystalline siliceous materials, such as mordenite or Zeolite Y described in U.S. Pat. No. 3,130,007, silica gel is known as a catalyst component. However, unlike these crystalline materials, silica gel is not itself catalytically active. Instead, silica gel is most frequently used in catalysts as a relatively inert support material upon which any of a number of catalytically active metals are deposited.

Despite its usual inertness, some attempts have been made to produce reactive silicas. Among these are the achievements of M. J. D. Low and H. Mark, who have authored several articles directed to silicas of improved chemisorption properties produced by treating conventional silicas with various chemical agents (for instance, trimethoxymethane and certain dienes). The articles of Low an Mark relating to reactive silicas include "Reactive Silica VIII. Methoxylation of Silica Using Trimethoxymethane" set forth in the *Journal of Catalysis*, Vol. 44, pp. 300 to 305 (1976), "Reactive Silica X. Ethylene Sorption and Polymerization" set forth in the *Journal of Catalysis*, Vol. 48, pp. 104 to 110 (1977), and "Reactive Silica XII. The Sorption and Polymerization of Several Alkenes" set forth in the *Journal of Catalysis*, Vol. 50, pp. 373 to 378 (1977). M. J. D. Low has also authored a paper relative to reactive silicas in conjunction with A. G. Severdia entitled "Reactive Silica XIII. Activation of Silica by Pyrolizing Chemisorbed $HSiCl_3$" as set forth in the *Journal of Catalysis*, Vol. 54, pp. 219 to 222 (1978).

The efforts of the art with respect to silica gels have not resulted in a commercially attractive silica gel having highly catalytic properties. From the viewpoint of commercial preparation, it would be especially desirable if not only a silica gel of highly active catalytic properties were available but also a method of preparing such a silica gel without resorting to either expensive and/or corrosive chemicals or preparations involving conversion of inactive silica gels to a catalytically active form. More specifically, it would be desirable if a direct preparation method were available for producing a catalytically active silica gel without the necessity for the intermediate formation of an inactive silica gel.

Accordingly, it is a major object of the present invention to prepare a novel amorphous silica of high catalytic activity, particularly in the form of silica gel, and to do so directly, without the necessity for converting an inactive silica gel to an active form. It is a further object of the invention to provide chemical processes wherein the silica gel of the invention is utilized to catalytically promote one or more chemical reactions. It is yet another object of the invention to prepare the silica gel of the invention with relatively inexpensive and noncorrosive chemicals. It is yet another object to provide a novel silica hydrogel, which, upon heating, or upon washing followed by heating, yields the catalytically active silica gel of the invention. These and other objects will become more apparent to those skilled in the art in light of the following description of the invention.

SUMMARY OF THE INVENTION

It has now been discovered that highly catalytically active amorphous silicas are derivable from a reaction mixture containing as the essential ingredients water, silicate anions, and an organic reactant selected from the group consisting of amines having a $pK_a$ above 10, quaternary ammonium cations and quaternary phosphonium cations wherein a nitrogen or phosphorus atom, respectively, is bonded to four carbon atoms, precursors of the foregoing, and mixtures thereof. Under suitable conditions, the reaction mixture yields a hydrogel or precipitate of silica, from which the amorphous silica of the invention may be produced by drying or calcining if the hydrogel or precipitate is relatively free of deleterious alkali or alkaline earth metals, or, if not, the desired silica may be produced by removing the deleterious metals and then drying or calcining.

The amorphous silica of the invention is useful in catalysis, particularly where the promotion of acid-catalyzed chemical reactions is required, as for example in the cracking of hydrocarbons or the isomerization of o-xylene. The catalytic properties of the present silica may be enhanced by the addition of other catalytic agents, as for example by admixture with a zeolite or impregnation of a metal component.

DETAILED DESCRIPTION OF THE INVENTION

The present invention is, in its preferred embodiment, directed to highly catalytically active silica gels prepared from certain aqueous silicate reaction mixtures. The initial aqueous solution contains silicate anions, usually and most conveniently prepared by dissolving sodium silicate in an aqueous liquid, such as distilled or deionized water. Other water-soluble silicate anion precursors may be used, as for example, potassium silicate. In addition, ammonium silicate is a suitable precursor and may be prepared by ammonium ion-exchanging a solution of sodium or potassium silicate utilizing known ion exchange techniques. Other sources of silicates may also be employed, and, in general, water-soluble monosilicates and polysilicates will prove useful, and so also will mono- and polysilicic acids, as will various mixtures of silicates and/or silicic acids.

The aqueous solution is generally prepared so as to have a concentration of silicate ions such that the maximum possible amount of silica producible therefrom is about 2 to 30 percent by weight, calculated as $SiO_2$, preferably from 5 to about 15 percent by weight. A most convenient and highly preferred silicate solution is prepared by diluting N Brand sodium silicate obtainable from the Philadelphia Quartz Company with water in a volumetric ratio between about 1:3 and 1:6, N Brand solution to water.

In addition to water and silicate anions, the reaction mixture is further provided with an organic reactant selected from the group consisting of the amines of $pK_a$ above 10, quaternary ammonium cations wherein a nitrogen atom is bonded to four carbon atoms, quaternary phosphonium cations wherein a phosphorus atom is bonded to four carbon atoms, precursors of the foregoing, and mixtures thereof. The more useful organic reactants added to the silicate solution are readily soluble in water, but even reactants which are only slightly soluble in water are effective, especially when a suitable emulsifying agent is added to the reaction mixture followed by vigorous stirring.

Suitable organic reactants for use in the invention include, for example, ethylenediamine and pyrrolidine, but far more preferable are organic reactants which introduce into the reaction mixture a quaternary ammonium ion wherein a nitrogen atom is bonded to four carbon atoms. The more preferred quaternary ammonium ions contain four alkyl groups linked to a nitrogen atom, and more preferably still, all four alkyl groups contain between one and six carbon atoms, and most preferably between two and four carbon atoms, with the most preferred alkyl groups being n-propyl and n-butyl. In a specific embodiment of the invention, quaternary ammonium cations are introduced into the reaction mixture through the aid of precursors, usually by the addition of one or more alkyl salts containing one to four carbon atoms plus a tertiary amine containing a nitrogen atom bonded to three alkyl groups each having between one and six carbon atoms. For example, in the preferred embodiment, the quaternary ammonium ions are produced by adding n-propyl bromide, n-butyl bromide, and tri-n-propylamine to the reaction mixture. Alternatively, however, and assuming a relatively high pH in the reaction mixture (e.g., above about 10), the required quaternary ammonium cation may be produced by adding either ammonia or a primary or secondary amine to the reaction mixture, along with one or more alkyl compounds, such as an alkylhalide, an alkylsulfate, etc. In yet another embodiment of the invention, the quaternary ammonium ions are produced via addition of a water-soluble quaternary ammonium compound, as for example by the addition of a compound containing a chloride, bromide, iodide, or sulfate anion and, as the cation, tetramethylammonium ion, tetraethylammonium ion, a tetrapropylammonium ion, a tetrabutylammonium ion, a diethyldipropylammonium ion, a triethylmonobutylammonium ion, and similar quaternary ammonium cations. One such water-soluble quaternary ammonium compound is prepared in an aqueous alkaline liquid by adding a source of ammonium and/or alkylated ammonium cations, plus sufficient of one or more alkylhalides to replace all the hydrogen atoms, if any, which are attached to the nitrogen atom of the ammonium or alkylated ammonium cations, from which a tetraalkylammonium hydroxide is recovered.

The reaction mixture of water, silicate anion, and organic reactant may be prepared in any convenient manner, there being no criticality in the order of mixing. The reaction mixture, however, will generally contain between 20 and 200 moles of water, and preferably between 40 and 100 moles of water, per atom of silicon present in the form of mono- and polysilicic acids and mono- and polysilicates. In addition, the molar ratio of water to nitrogenous reactants plus phosphorous reactants ranges from 50 to 1 to 500 to 1, preferably from 100 to 1 to 250 to 1, reactants being the amines or quaternary cations specified hereinbefore, or their precursors.

The reaction mixture containing the silicate anion and suitable organic reactant(s) is, in the preferred embodiment, further provided with an organic solvent having mutual solubility with respect to water and the organic reactant(s). Typically, an oxygenated organic solvent is utilized for this purpose, with methylethylketone being preferred. The amount of the methylethylketone or other organic solvent added to the reaction mixture is between about 0 and 0.10 moles per mole of water, preferably between 0.002 and 0.010 moles per mole of water.

The addition of an organic solvent is especially appropriate when one or more of the reactants added to the reaction mixture are not readily soluble in water. For example, most alkyl halides are only slightly soluble in water, and an added organic solvent, such as methylethylketone, serves as an emulsifying agent, hastening the dissolution of alkyl halide reactants, particularly when accompanied by vigorous agitation.

The formation of a hydrogel from the reaction mixture is most readily favored at a pH below 12.0, usually in a range of 8 to 12, preferably 10 to 12. Accordingly, if the pH of the mixture is not favorable for reaction, then a suitable alkaline or acidic agent is added to drive the pH into the desired range. For example, if the reaction mixture initially has a pH above about 12, the chemical reactions producing the gel are favored by lowering the pH below 12, as for example, by introduction of an acid (i.e., acidification) or by ion exchange of some metal or ammonium cations in the reaction mixture for hydrogen ions.

Once the reaction mixture is at a suitable pH, initiation of the chemical reactions producing the hydrogel is commenced, which reactions are believed to involve polymerization and condensation mechanisms. However, to avoid the formation of a crystalline product, the reaction mixture should be maintained under relatively low temperature conditions favoring the formation of at least some amorphous hydrogel product, and preferably so as to obtain a product consisting essentially of an amorphous hydrogel. In order to achieve these results, temperature conditions are normally maintained below about 100° C., and are usually maintained at temperatures above 0° but below about 100° C., with the temperature usually being maintained between 20° and 95° C., and preferably between 50° and 85° C.

After adjusting the pH to a desired value, the reaction mixture is aged a sufficient length of time to allow a gel to form in a mother liquor, usually by syneresis. The time required for aging is dependent on a number of factors, including the temperature of reaction, the nature and concentration of the ingredients in the reaction mixture, and the pH of the reaction mixture. Usually, under pH conditions between 10 and 12, at least ten hours are required for gel formation, and time periods of 24 to 200 hours are typical while 48 to 100 are most usual.

After the hydrogel is prepared by the foregoing or equivalent methods, it is separated from the mother liquor, as by filtration, and if prepared from a reaction mixture rich in alkali or alkaline earth metal cations, the hydrogel is washed free of such metals, for example, by washing with an ammonium salt solution. The metals may also be removed by other methods, but however the removal is carried out, the resulting metals content, and particularly the alkali metals content, of the hydrogel is such that, upon dehydration, the contained metals will not interefere with the formation of the desired silica gel, and most especially, with its desired catalytic activity. In general, the hydrogel is washed such that no more than 0.010 atoms of total alkali metal remain for each atom of silicon. (Of course, one can avoid the removal of metals entirely by initiating the chemical reactions producing the hydrogel in a metals-free reaction mixture, but usually this is far less convenient than preparation in, for example, a solution containing dissolved sodium silicate.)

Subsequent to preparation of the hydrogel, it is dried and/or calcined so as to produce the silica gel of the invention by dehydration. In the preferred embodiment of the invention, the dehydration is effectuated by calcining the hydrogel at temperatures above 900° F. for twenty minutes to two hours. The resulting silica gel product is, preferably, essentially completely amorphous, is usually granular, and generally has a surface area between about 75 and 350 m²/gm, with even higher surface areas falling within the scope of the invention. In addition, the silica gel has a total metal to silicon atom ratio similar to that of the washed hydrogel, and usually also a similar distribution of metals, so that the alkali metal to silicon atom ratio of the washed hydrogel and that of the silica gel will be substantially the same.

The silica gel of the present invention has been found to have high catalytic activity with respect to the promotion of organic chemical reactions, as for example, in isomerizing ortho-xylene to para-xylene and meta-xylene and in cracking hydrocarbons into product hydrocarbons of lower average molecular weight and lower average boiling point. Although the invention is not limited to any theory of operation, these catalytic properties are believed due to the presence of strong acidic sites on the gel surface, which in turn is believed due to the presence of far fewer silanol groups on the gel surface than is the case with the relatively inactive amorphous silicas of the prior art. The paucity of silanol groups is also believed to impart hydrophobic and oil-adsorption properties, as for example from contaminated waters, to the amorphous silicas of the invention.

Although the present silica gel may be used for catalytic purposes without the further addition of catalytic agents, it is often desirable to combine an active component with the present silica gel and in so doing increase its suitability for a particular catalytic process. For example, if increased cracking activity is required, the silica gel can be admixed with a cracking component, as by dispersing into the gel a hydrogen Y zeolite containing one or more stabilizing rare earth elements. In this embodiment of the invention, the zeolite, usually in powder form, is mulled into the hydrogel from which the silica gel of the invention is to be subsequently obtained by dehydration or by washing followed by dehydration. Alternatively, if hydrogenation activity is required, a suitable Group VIB and/or Group VIII metal component may be deposited on the silica gel, typically by impregnation followed by consecutive calcination and sulfiding treatments to produce a catalyst having hydrocracking activity. To improve the hydrocracking properties, the catalyst may contain both a suitable hydrogenation component and a zeolite in addition to the silica gel. For hydrocracking, a stabilized Y zeolite will generally be a preferred choice, and for a selective form of hydrocracking known as hydrodewaxing, wherein the catalyst is especially selective for cracking straight chain and slightly branched chain paraffins, one may utilize a ZSM-5-type zeolite, or, more preferably, one may employ a non-zeolitic material known as silicalite, a crystalline silica polymorph disclosed in U.S. Pat. No. 4,061,724, herein incorporated by reference in its entirety. Silicalite is especially useful for hydrodewaxing when used in conjunction with nickel-tungsten hydrogenation components.

It is especially preferred in the preparation of catalysts from the silica gel of the invention that the silica gel be admixed with suitable binding agents to produce sols, pastes, or slurries from which catalytic particulates of sufficient strength and abrasion resistance for use in large reactor vessels may be produced. Examples of suitable binders include aluminas, silicas, and clays. Especially preferred, however, are peptized boehmite, acid-washed clays, and silicas such as bentonite, montmorillomite, halloysite, attapulgite, and magadiite. These binders can be combined with the catalytically active silica of the invention by mulling or slurrying followed by extruding or spray drying. Further catalytic components, such as a Group VIB metal and/or Group VIII metal component added for hydrogenation activity, may be incorporated with the binder-active silica mixture. This may be accomplished by direct addition of a suitable precursor of the desired metal catalytic component to the mulled or slurried mixtures followed by shaping and calcination; alternatively, the binder-active silica mixture may first be shaped and then successively calcined, impregnated with the chosen precursor or precursors, and calcined again. Yet other catalytic components may be incorporated into the binder-active silica mixture, as for example a zeolite for added cracking activity.

When utilized as a catalyst or a catalyst component, the silica gel of the invention is employed under conditions known to be effective for the intended purpose. In general, elevated temperatures and/or pressures are required. For example, in the cracking of hydrocarbons, elevated temperatures above about 900° F. are usually employed. Where a hydrogenation function is also desired, as for example in hydrocracking or hydrodewaxing, the presence of hydrogen is required, and usually an elevated pressure above about 500 p.s.i.g.

In the following Examples, the preparation of the silica gel of the invention and processes involving its use as a catalyst are described. The Examples, however, are for the purpose of illustration only and are not intended to limit the invention, which is defined by the claims.

EXAMPLE I

In this Example, a silica gel is prepared in accordance with the invention, and its catalytic properties for isomerizing ortho-xylene are demonstrated.

A solution is prepared having the following components: 512 ml. of water, 139 g. of "N" Brand sodium silicate solution (containing 28.9% by weight $SiO_2$ and 8.9% by weight $Na_2O$), 8.7 g. of n-propyl bromide, 8.5 g. of n-butyl bromide, 19.1 g. of tri-n-propylamine, and 40.3 g. of methylethylketone. The solution is then acidified to a pH of 11.0 by the addition of 6N acetic acid, after which the solution is allowed to stand for 64 hours at 79° C. A gel forms in the solution, and after separation from the mother liquor having a pH of 11.3, the gel is washed with distilled water, dried, exchanged three times with a solution of 10% by weight ammonium nitrate to remove the exchangeable sodium cations, and finally calcined in air at 1200° F. for two hours, producing a granular product.

The granular silica gel is given the designation Y-2822A and found to have a surface area of 112 $m^2/gm$. When tested with dicinnamalacetone and triphenylcarbinol indicators, high acidity is indicated. In addition, X-ray diffraction analysis determines that the granules are essentially amorphous in nature and not crystalline. The granules are screened to collect a 20/40 mesh fraction for catalytic testing.

A comparative experiment is then performed to demonstrate the catalytic activity of the Y-2822A silica gel, prepared in accordance with the invention, against a conventional silica gel. The conventional silica gel is Davison No. 12 having a mesh size of 28/40 and a surface area of 695 $m^2/gm$. Each gel is then tested as follows: hydrogen and ortho-xylene in a 2:1 mole ratio are passed over 1.70 gram samples of the silica gels at atmospheric pressure and at a weight hourly space velocity of 2.1 in the case of the Y-2822A silica gel and 1.6 for the conventional silica gel. The results obtained at varying operating temperatures are summarized in the following Table I:

TABLE I

| | Catalyst | | | | | |
|---|---|---|---|---|---|---|
| | Silica Gel of Invention | | | | Davison No. 12 Silica Gel | |
| Hours on Stream | 1 | 2 | 3 | 4 | 1 | 2 |
| Operating Temperature, °F. | 600 | 700 | 800 | 900 | 700 | 900 |
| Space Velocity, WHSV | 2.1 | 2.1 | 2.1 | 2.1 | 1.6 | 1.6 |
| Product Color | Yellow | Yellow | Yellow | Yellow | Clear | Clear |
| Product Distribution,[1] | | | | | | |
| m-xylene | 0.00 | 0.27 | 4.36 | 14.2 | 0.00 | 0.08 |
| p-xylene | 0.00 | 0.00 | 0.13 | 0.66 | 0.00 | 0.00 |
| Total Conversion | 0.00 | 0.27 | 4.49 | 14.9 | 0.00 | 0.08 |
| Specific Rate[2] × $10^{10}$ | <0.001 | 0.080 | 1.33 | 4.39 | <0.001 | 0.003 |

[1] The product distribution is determined as millimoles of product per mole of feed.
[2] The specific rate is a measure of the activity of the catalyst to promote a given reaction, in this case, the conversion of o-xylene to total p-xylene and m-xylene products. The specific rate is an indication of the number of molecules of reactant which are converted per second per unit area of surface area of catalyst. In the present case, the specific rate is calculated by reference to the following equation:

$$\text{Specific Rate} = \frac{\text{(Moles Converted)}}{\text{(WHSV) Per Mole of Feed) }(6.02 \times 10^{23})}{3.6 \times 10^7 \text{ (Surface Area, m}^2/\text{g)} \text{ (Molecular Weight of Reactant)}}$$

with the resulting value being in terms of the number of molecules of o-xylene converted per second per square centimeter of surface area.

The data in the foregoing Table I indicate that the silica gel of the invention is much more highly active than conventional silica, yielding at 900° F. over 185 times as much para-xylene plus meta-xylene. These results are especially surprising in view of the fact that the silica gel of the invention is prepared with a much reduced surface area and is utilized at a higher space velocity. Both of these features should have worked to the disadvantage of the Y-2822A silica gel composition, yet it proves far more active for isomerization reactions.

It will also be noted in the data in Table I that, as indicated by the difference in specific rates at 900° F., the silica gel of the invention is more than 1200 times as catalytically active as the conventional silica gel for the isomerization of o-xylene to total p-xylene and m-xylene products. At 900° F. operating temperature, the specific rate for the silica gel of the invention for isomerizing o-xylene will usually be such that at least $1.0 \times 10^{10}$, more usually at least $2.0 \times 10^{10}$, preferably at least $3.0 \times 10^{10}$, and most preferably (as evidenced by the data of Table I) at least $4.0 \times 10^{10}$ molecules of o-xylene are converted per second per square centimeter of catalytic surface area.

EXAMPLE II

In this Example, a silica gel prepared in accordance with the invention is shown to have catalytic cracking activity for converting hydrocarbons into lower boiling products.

A sample of the Y-2822A silica gel of the invention, prepared as described in Example I, is utilized in a continuous process for cracking a heavy naphthenic hydrocarbon oil having the following properties:

TABLE II

| | |
|---|---|
| Specific Gravity 60/60 | 0.89 |
| Initial Boiling Point | 580° F. |
| Vol. % Boiling below 700° F. | 4.6 |
| Vol. % Boiling below 1000° F. | 96.6 |

The operating conditions are as summarized in Table III:

TABLE III

| | |
|---|---|
| Operating Temperature, °F. | 900° F. |
| Space Velocity, WHSV | 8.0 |
| Catalyst to Feedstock Wt. Ratio | 4.0 |

The distribution of products obtained are summarized in the following Table IV, with it being noted that the temperature ranges given for the liquid products are the true boiling ranges for such products at atmospheric pressure.

TABLE IV

| Gas Production | 190 SCF/bbl |
|---|---|
| Light Liquid, x–180° F. | 11.3 vol. % |
| Gasoline, 180°–420° F. | 22.0 vol. % |
| Turbine Fuel, 300°–550° F. | 12.0 vol. % |
| Furnace Oil, 300°–700° F. | 19.3 vol. % |

These data clearly indicate that the silica gel of the invention has substantial catalytic cracking activity.

In the foregoing discussion, the primary attention has been directed to silica gels, and this for the reason that silica gel is the preferred form of the amorphous silica of the invention. However, other forms of amorphous silica may be prepared in accordance with the invention, as for example precipitated silica. Precipitated silica is an amorphous silica produced, as its name implies, by a chemical reaction involving precipitation, usually as a result of destabilizing an aqueous silicate solution. Destabilization can be effected by adding flocculents or precipitating agents which tend to decrease the surface charge on silica. For example, the reaction mixture may be heated, mixed with a precipitating agent such as sodium carbonate, and then cooled to precipitate silica at high pH. Fluoride salts may similarly serve as precipitating agents, as also may certain water-soluble organic solvents such as acetone and alcohols, particularly at high pH. In addition, polyvalent cations can be used as flocculating agents to promote precipitation. For example, barium and/or calcium can be used to precipitate fine particles of silica.

In the invention, the foregoing procedure is modified such that the precipitate is formed in the presence of one or more of the organic reactants hereinbefore described in fuller detail. In other words, the reaction mixture for producing precipitated silica is of similar composition to those described hereinbefore with respect to the preparation of silica gel except that it further contains one or more flocculating and/or precipitating agents which induce the formation of a silicon-containing precipitate as opposed to a silicon-containing hydrogel. The flocculating and/or precipitating agent is added in an amount sufficient to effect the precipitation, which may occur instantaneously or require up to about two hours for completion. After the precipitate is formed, it is separated from the mother liquor and, if necessary, washed free of detrimental metals, particularly alkali and/or alkaline earth metals. The washing may be carried out without any aqueous solution, but solutions of an acid such as nitric acid or an ammonium salt such as ammonium nitrate or ammonium carbonate are preferred. The washing is preferably carried out to a degree such that the precipitate contains less than 0.010 atoms of total alkali and alkaline earth metals to each atom of silicon. The washed precipitate is then dried and/or calcined to the desired degree of dehydration, resulting in a precipitated silica of the invention.

Although the invention has been described in conjunction with embodiments thereof, including a preferred embodiment, it is apparent that the invention is capable of many modifications, alternatives, and variations. For example, in one embodiment of the invention, instead of preparing the silica gel from a reaction mixture having a pH between the usual values of 8 and 12, one may prepare the silica gel from reaction mixtures of lower pH, even acidic pH's, such as from about 1 to 5. This embodiment of the invention has the advantage of relatively rapid formation of the silica gel, requiring little aging time in most instances, and in many others, essentially none. In effect, the gel precipitates almost as soon as it forms, the rate of formation increasing with decreasing pH's. Accordingly, it is intended to embrace within the invention all such modifications, alternatives, and variations as may fall within the spirit and scope of the appended claims.

We claim:

1. An isomerization process comprising contacting a hydrocarbon comprising ortho-xylene under isomerization conditions including an elevated temperature with a catalyst prepared by a method comprising forming a hydrogel or precipitate in a reaction mixture comprising water, silicate anions and an organic reactant selected from the group consisting of amines having a $pK_a$ value above about 10.0, quaternary ammonium cations having a nitrogen atom bonded to four carbon atoms, quaternary phosphonium cations having a phosphorus atom bonded to four carbon atoms, precursors of the foregoing and mixtures thereof, and dehydrating the resultant hydrogel or precipitate to yield a product containing amorphous silica, said isomerization conditions are such that at least a portion of said ortho-xylene is converted to para-xylene or meta-xylene.

2. The process defined in claim 1 wherein said isomerization conditions include a temperature above about 700° F.

3. The process defined in claim 1 wherein said catalyst further comprises at least one binding agent selected from the group consisting of aluminas, silicas and clays.

4. The process defined in claim 1 wherein said contacting is in the presence of hydrogen.

5. The process defined in claim 1 wherein said organic reactant is a quaternary ammonium cation and said carbon atoms in said quaternary ammonium cation are each members of alkyl groups containing between 1 and 6 carbon atoms.

6. The process defined in claim 1 wherein the pH of the reaction mixture is between about 8 and 12 and wherein the reaction mixture producing said hydrogel is maintained below 100° C.

7. An isomerization process comprising contacting a hydrocarbon comprising ortho-xylene under isomerization conditions with a catalyst prepared by a method comprising forming a hydrogel in a reaction mixture comprising water, silicate anions and quaternary ammonium cations having a nitrogen atom bonded to four carbon atoms, and dehydrating the hydrogel to yield a product containing a substantial proportion of amorphous silica gel, said isomerization conditions are such that at least a portion of said ortho-xylene is converted to para-xylene or meta-xylene.

8. The process defined in claim 7 wherein said isomerization conditions include a temperature above about 700° F.

9. The process defined in claim 7 wherein said catalyst further comprises at least one binding agent selected from the group consisting of aluminas, silicas and clays.

10. The process defined in claim 7 wherein said contacting is in the presence of hydrogen.

11. The process defined in claim 7 wherein said quaternary ammonium cation is introduced into said reaction mixture by addition of one or more precursors thereof, said precursors being selected from the group consisting of (1) quaternary ammonium compounds containing a nitrogen atom bonded to four carbon atoms and having at least some solubility in water and (2) amines or ammonia in combination with an emulsifying agent and one or more alkyl compounds containing a halide or sulfate, said alkyl compounds being present in an amount at least sufficient to bond at least one nitrogen atom of the amines or ammonia to four carbon atoms.

12. The process defined in claim 7 wherein the pH of the reaction mixture is between about 8 and 12 and wherein the reaction mixture producing said hydrogel is maintained below 100° C.

13. An isomerization process comprising contacting a hydrocarbon comprising ortho-xylene in the presence of hydrogen under isomerization conditions with a catalyst prepared by a method comprising acidifying a reaction mixture comprising sodium silicate, water and a quaternary ammonium cation having a nitrogen atom bonded to four carbon atoms, allowing a hydrogel to form in the reaction mixture, separating the hydrogel from the reaction mixture and removing one or more metals from said hydrogel, and dehydrating said hydrogel to produce a product containing a substantial proportion of amorphous silica gel, said isomerization conditions are such that at least a portion of said ortho-xylene is converted to para-xylene or meta-xylene.

14. The process defined in claim 13 wherein said catalyst further comprises a binding agent selected from the group consisting of peptized boehmite, acid-washed clays, bentonite, montmorillomite, halloysite, attapulgite and magadiite.

15. The process defined in claim 13 wherein said isomerization conditions include a temperature above about 700° F.

16. The process defined in claim 13 wherein said reaction mixture contains sodium as essentially the only alkali or alkaline earth metal therein, and after said sodium removal, said hydrogel contains sodium to silicon in an atom ratio less than about 0.10.

17. The process defined in claim 13 wherein said acidifying produces in the reaction mixture a pH between about 10 and 12, and during the formation of said hydrogel, the reaction mixture is maintained at a temperature below 100° C.

18. An isomerization process comprising contacting a hydrocarbon comprising ortho-xylene under isomerization conditions with a catalyst prepared by a method comprising (a) forming a hydrogel in a reaction mixture comprising water, silicate anions and a quaternary ammonium cation having a nitrogen atom bonded to four carbon atoms, said quaternary ammonium cation is introduced into said reaction mixture by addition of one or more precursors thereof, said precursors being selected from the group consisting of (1) quaternary ammonium compounds containing a nitrogen atom bonded to four carbon atoms and having at least some solubility in water and (2) amines or ammonia in combination with an emulsifying agent and one or more alkyl compounds containing a halide or sulfate, said alkyl compounds being present in an amount at least sufficient to bond at least one nitrogen atom of the amines or ammonia to four carbon atoms, and (b) dehydrating the hydrogel to yield a product containing a substantial proportion of amorphous silica gel, said isomerization conditions are such that at least a portion of said ortho-xylene is converted to para-xylene or meta-xylene.

19. The process defined in claim 18 wherein said isomerization conditions include a temperature above about 700° F. and the presence of hydrogen.

20. An isomerization process comprising contacting a hydrocarbon comprising ortho-xylene under isomerization conditions with an amorphous silica, said amorphous silica having catalytic activity for isomerizing ortho-xylene to para-xylene and meta-xylene at 900° F. and atmospheric pressure at a rate of at least $1.0 \times 10^{10}$ molecules of ortho-xylene converted per second per square centimeter of surface area of said amorphous silica.

21. The process defined in claim 20 wherein said contacting is in the presence of hydrogen.

22. The process defined in claim 20 wherein said catalyst further comprises at least one binding agent selected from the group consisting of aluminas, silicas and clays.

23. An isomerization process comprising contacing a hydrocarbon comprising ortho-xylene under isomerization conditions with a composition consisting essentially of an amorphous silica gel, said amorphous silica gel having catalytic activity for isomerizating ortho-xylene to para-xylene plus meta-xylene at 900° F. and atmospheric pressure at a rate of at least $4.0 \times 10^{10}$ molecules of ortho-xylene converted per second per square centimeter of surface area of said composition.

24. The process defined in claim 23 wherein said contacting is in the presence of hydrogen.

25. The process defined in claim 23 wherein said catalyst further comprises a binding agent selected from the group consisting of peptized boehmite, acid-washed clays, bentonite, montmorilliomite, halloysite, attapulgite and magadite.

* * * * *